United States Patent [19]
Capetan et al.

[11] Patent Number: 5,282,852
[45] Date of Patent: Feb. 1, 1994

[54] METHOD OF CALCULATING THE REQUIRED POWER OF AN INTRAOCULAR LENS

[75] Inventors: Thomas G. Capetan, Corona Del Mar; T. Scott Rowe, Mission Viejo, both of Calif.

[73] Assignee: Alcon Surgical, Inc., Fort Worth, Tex.

[21] Appl. No.: 939,213

[22] Filed: Sep. 2, 1992

[51] Int. Cl.$^5$ .............................................. A61F 2/16
[52] U.S. Cl. ....................................................... 623/6
[58] Field of Search ........................................... 623/6

[56] References Cited

U.S. PATENT DOCUMENTS

| | | | |
|---|---|---|---|
| 4,710,193 | 12/1987 | Volk | 623/6 |
| 5,092,880 | 3/1992 | Ohmi | 623/6 |
| 5,123,921 | 6/1992 | Werblin et al. | 623/5 |

OTHER PUBLICATIONS

Article entitled *SRK/T betters SRK formula for IOL power prediction in unusually long eyes*, Donald R. Sanders, M.D., Ph.D., Ocular Surgery News—vol. 7, No. 8, pp. 1, 24 and 26, Apr. 15, 1989.

Article entitled *Development of the SRK/T Intraocular Lens Implant Power Calculation Formula*, John A. Retzlaff, M.D., Donald R. Sanders, M.D., Ph.D., and Manus C. Kruff, M.D., J. Cataract Refract. Surg.—Vol. 16, May, 1990.

Article entitled *Prediction of Intraocular Lens Position After Cataract Extraction*, Thomas Olsen, M.D., J. Cataract Refract. Surg.—Vol. 12, Jul. 1986, pp. 376–379.

*Manual of Implant Power Calculation Including SRK II Formula Section Edition*, John Retzlaff, M.D., Donald Sanders, M.D., Ph.D. and Manus Kraff, M.D., 1988.

*Primary Examiner*—Randall L. Green
*Assistant Examiner*—Elizabeth M. Burke
*Attorney, Agent, or Firm*—Jeffrey S. Schira

[57] ABSTRACT

A method of calculating the required power of an intraocular lens to be implanted in an eye having the steps of measuring the axial length, preoperative anterior chamber depth and natural lens thickness of the eye, measuring and averaging corneal radii of curvature along a first axis and along a second axis normal to the first axis, calculating a lens locator constant from the axial length and the averaged corneal radii of curvature using a quadratic surface equation, determining a postoperative anterior chamber depth using the measured preoperative anterior chamber depth, the measured natural lens thickness and the calculated constant and calculating the required power of the intraocular lens and the predicted postoperative refraction using the postoperative anterior chamber depth.

3 Claims, 1 Drawing Sheet

METHOD OF CALCULATING THE REQUIRED POWER OF AN INTRAOCULAR LENS

BACKGROUND OF THE INVENTION

The present invention relates to intraocular lenses in general and specifically to methods of calculating the required power of an intraocular lens.

Intraocular lenses (IOL's) are commonly used to replace a diseased natural lens in the human eye. The first IOL implant was done in November 1949 without the benefit of the many accurate and now commercially available IOL implant power formulas. The result was a $-24.0$ diopter myopic refractive error. Continuous experimentation produced a standard IOL implant power that gave marginal refractive results over a statistically significant population base. This practice prevailed until the late 1960s when Fyodorov published a formula in Russian for determining IOL implant powers based on geometrical optics and data from A-scans and keratometers. Colenbrander published the first formula written in English in 1973. See M. C. Colenbrander, *Calculation of the Power of an Iris-Clip Lens for Distance Vision*, Br. J. Ophthal. 57:735-40, (1973). Concurrent with the commercial development of the A-scan biometer in the early 1970s, Binkhorst published several papers on IOL power calculations. In the mid-1970s the Santa Monica Intraocular Lens Calculation Lab was established, using modification to the Colenbrander formula made by Hoffer. See C. D. Binkhorst, *Power of the Pre-Pupillary Pseudoshakos*, B.J.O. 56:332-37, (1972). In 1980 Sanders, Retzlaff and Kraff pooled their data and defined a regression-based formula, the SRK formula. This formula has been continuously expanded and updated, enjoys widespread popularity and has been adapted to many different IOL's through the A constant.

With the onset of posterior chamber lenses, the SRK regression formula continued to prove useful for average axial length eyes, but tended to predict too small an emmetropia value in short eyes and too large a value in larger eyes. The first generation theoretical formulas tended to do the opposite with the axial length extremes. The second generation SRK/T formula was designed to provide more accurate emmetropic and ametropic IOL power prediction at the axial length extremes, while not sacrificing accuracy for average eyes. See J. Retzlaff, D. R. Sanders & M. C. Kraff, *Development of the SRK/T Intraocular Lens Implant Power Calculation Formula*, J. Cataract & Refractive Surg. 16(3):333-40, (1990). The regression based SRK formula was also modified to better span a wide range of eyes, and has re-appeared as the SRK II. See D. R. Sanders, J. Retzlaff & M. C. Kraff, *Comparison of the SRK II Formula and the Other Second Generation Formulas*, J. Cataract & Refractive Surg. 14(3):136-41, (1988). Meanwhile, Olsen (see T. Olsen, *Theoretical Approach to IOL Calculation Using Gaussian Optics*, J. Cataract & Refractive Surg. 13:141-45, (1987)), Holladay, et al. see J. T. Holladay, T. C. Praeger, T. Y. Chandler & K. H. Musgrove, *A Three-Party System for Refining Intraocular Lens Power Calculations*, J. Cataract & Refractive Surg. 14:17-24, (1988)) and Thompson, et al. see J. T. Thompson, A. E. Maumenee & C. C. Baker, *A New Posterior Chamber Intraocular Lens Formula for Axial Myopes*, Ophthal. 91:484-88, (1984)) have all described second generation theoretical formulas that make use of more measured data.

In computing the required IOL power, estimating the location of the implanted lens within the eye is critical. Modern ultrasonic imaging equipment, such as the A-scan biometer, are quite accurate in determining the preoperative anterior chamber depth ("$ACD_{pre}$") (the distance between the anterior surface of the cornea and the anterior surface of the natural lens). However, $ACD_{post}$ (the distance between the anterior surface of the cornea and the principal refracting plane of the IOL) is the critical dimension in determining the implanted power of the IOL and will differ from $ACD_{pre}$ because IOL's generally are thinner than natural lenses and lens designs vary, for example, different lenses use different amounts of vaulting. Vaulting is the axial displacement of the IOL from the center of the capsular bag produced by the spring forces in the contracted IOL haptics. $ACD_{post}$ by definition cannot be determined until after the IOL has been implanted and must be estimated from $ACD_{pre}$. The accuracy of any IOL power formula is highly dependent on the measurements and methods used to estimate $ACD_{post}$.

Only one of these formulas, the SRK/T formula, uses the actual, A-scan biometer measured $ACD_{pre}$ to estimate $ACD_{post}$, and only one of these formulas has suggested using the A-scan measured thickness of the natural lens to estimate $ACD_{post}$. Instead, at least two of these formulas estimate $ACD_{post}$ from a computed corneal height. Olsen, in his $ACD_{post}$ formula, measures the limbus diameter of the cornea and computes corneal height from a spherical sag formula. The computed corneal height, $ACD_{pre}$ and natural lens thickness is used in a multiple regression analysis to predict $ACD_{post}$. See T. Olsen, *Prediction of Intraocular Lens Position After Cataract Extraction*, J. Cataract & Refractive Surg., 12:376-79, (July 1986). The SRK/T formula estimates corneal height from the average measurement of the patient's corneal radius of curvature made with a keratometer ("K reading"). Thompson and coworkers have discovered a strong correlation between the axial length of the eye and the averaged K readings, and have used that relationship to estimate $ACD_{post}$. See J. T. Thompson, A. E. Maumenee & C. C. Baker, *A New Posterior Chamber Intraocular Lens Formula for Axial Myopes*, Ophthal. 91:484-88, (1984). However, this relationship was shown only for myopic eyes.

While variances between the predicted and actual postoperative patient refractions have decreased with the onset of the second generation formulas discussed above, the Standard Error of Estimate is still greater than 0.8 diopters throughout the axial length range for one of the most widely used formula, the SRK/T formula. Also, greater than 2 diopter errors still occur while using this formula in approximately 3.3% of the cases. While these are excellent results historically, with the increase in cataract surgery volume, even this small percentage results in a significant patient base that still requires spectacle correction for far-field vision.

One of the primary factors leading to this relatively large Standard Error of Estimate is the use of the regressively determined A-constant. The A-constant is used to estimate the offset between the plane of the natural lens and the principal refracting plane of the implanted IOL and is specific to the particular style of IOL. For extremely long or short eyes, the SRK II and SRK/T formulae adjust the A-constant by adding or subtracting a correction factor. This adjustment can increase the potential error in predicting the required power of the IOL to be implanted.

Accordingly, a need continues to exist for a more accurate method of calculating the required power of an intraocular lens over a broad range of axial lengths.

BRIEF DESCRIPTION OF THE INVENTION

The present invention improves upon prior art methods of calculating the required power of an IOL by providing a method that uses an A-scan biometer to determine the axial length, preoperative anterior chamber depth and natural lens thickness. The inventors have found that a strong correlation exists between a combination of the thickness of the natural lens, $ACD_{pre}$, axial length, averaged K readings and the postoperative anterior chamber depth. Using the A-scan biometer to obtain the natural lens thickness and using this measured thickness in conjunction with the measured $ACD_{pre}$ and axial length to estimate the postoperative anterior chamber depth reduces the number of estimated constants and increases the accuracy of IOL implant power calculation, particularly for eyes having extremely short or long axial lengths.

Accordingly, one objective of the present invention is to provide a method of calculating the required power of an intraocular lens that uses fewer estimated constants.

Another objective of the present invention is to provide a method of calculating the required power of an intraocular lens that uses an A-scan biometer to obtain actual measurements of the intraocular distances used in calculating the required power of an intraocular lens.

Another objective of the present invention is to provide a method of calculating the required power of an intraocular lens that is more accurate.

These and other objectives and advantages of the method of the present invention will become apparent from the detailed description, drawings and claims that follow.

DETAILED DESCRIPTION OF THE INVENTION

The inventors of the present invention have postulated that the final postoperative principal plane of refraction of an implanted IOL will lie within the volume previously occupied by the natural lens. The location of the implanted IOL can be determined more accurately than in prior methods by measuring the natural lens thickness, adjusting the thickness to account for variables in IOL styles and individual eye measurements and adding the adjusted lens thickness to the preoperative distance between the anterior surface of the cornea and the central plane of the natural lens to determine the postoperative distance between the anterior surface of the cornea and the principal plane of refraction of the IOL. The adjustment to the lens thickness is accomplished through the use of a constant (the "J" constant) that is calculated through the use of a quadratic surface calculation and is specific to the individual and style of IOL.

Figure 1:
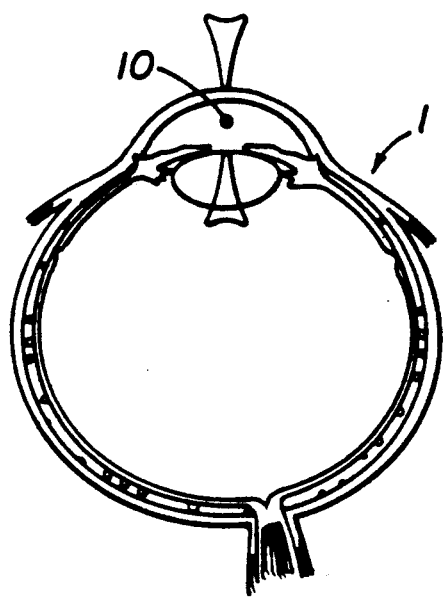
FIG. 1 is a representational cross section of the human eye illustrating the preoperative anterior chamber depth.

The method of the present invention requires that the intraocular distances and corneal curvature of the individual patient's eye 1 be measured. An A-scan biometer is used to measure the axial length ("AL"), preoperative anterior chamber depth 10 (see FIG. 1) ("$ACD_{pre}$") and natural lens thickness ("T") of the eye to receive the IOL. A keratometer is used to obtain the K readings (in diopters), that are averaged, ("$K_{ave}$") of the subject eye. The individual-specific J lens locator constant ("$J_{ind}$") can then be calculated using the following quadratic surface calculation:

$$J_{ind} = C_1 AL + C_2 AL^2 + C_3 K_{ave} + C_4 K_{ave}^2 + C_5 K_{ave} * AL + C_6$$

where constants $C_1$–$C_6$ are IOL specific and determined by regressive data fitting only after a statistically significant population of patients have been measured for natural lens thickness, axial length and K readings. Such polynomial curve fitting techniques are well-known in the art and can be found, for example, in Lancaster and Salkauskas, *Curve and Surface Fitting*, *(An Introduction)*, pp. 147–51 (Academic Press 1986).

Figure 2:
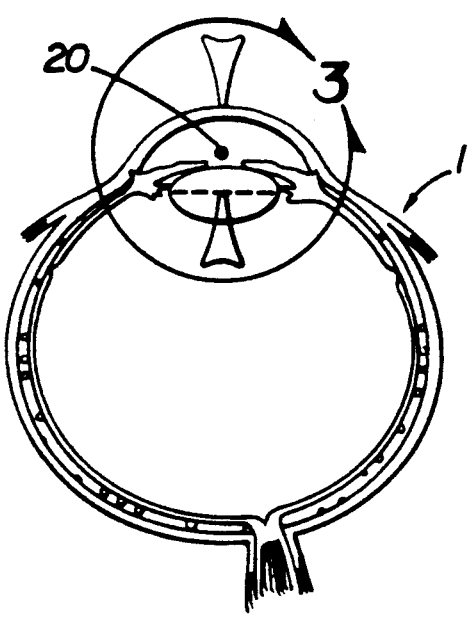
FIG. 2 is a representational cross section of the human eye similar to FIG. 1 illustrating the postoperative anterior chamber depth.

The J values used in the series of simultaneous equations for calculation of $C_1$–$C_6$ are determined prior to the regression analysis by noting the IOL type and power used in the aforementioned statistically significant patient population. Working backwards from the $IOL_{emme}$ power formula given below, $ACD_{post}$ 20 (see FIG. 2) can be determined iteratively. With $ACD_{pre}$ and T known for each patient, $J_{ind}$ can be determined for the solution set of the regression analysis.

Once $J_{ind}$ is calculated, $ACD_{post}$ can be determined using the following formula:

$$ACD_{post} = ACD_{pre} + T/J_{ind}$$

Figure 3:
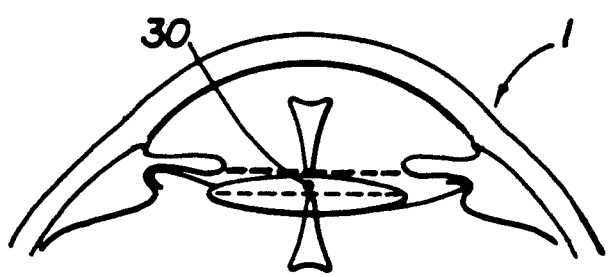
FIG. 3 is an exploded cross section of the anterior chamber of the human eye taken at circle 3-3 in FIG. 2, showing IOL vault.

As can be seen, $J_{ind}$, as well as $ACD_{post}$, are both individual and IOL specific, and the necessity of using an error-inducing correction factor to adjust $ACD_{post}$ to account for long or short axial length eyes is eliminated. In addition, both $J_{ind}$ and $ACD_{post}$ account for variation in vault 30 (see FIG. 3) between different styles of IOL's.

Using $ACD_{post}$, the emmetropia IOL power ("$IOL_{emme}$") and ametropia power ("$IOL_{amet}$") can be calculated using the following formulae:

$$IOL_{emme} = \frac{1000 * n_a * (n_a * r - n_c m1 * L_{opt})}{(L_{opt} - ACD_{post})(n_a * r - n_c m1 * ACD_{post})}$$

and $$IOL_{amet} = \frac{1000 * n_a * (n_a * r - n_c m1 * L_{opt} - .001 * R * V(n_a * r - n_c m1 * L_{opt}) + L_{opt} * r)}{(L_{opt} - ACD_{post})(n_a * r - n_c m1 * ACD_{post} - .001 * R * V(n_a * r - n_c m1 * ACD_{post} + ACD_{post} * r)}$$

where:

$L_{opt}$ = is the optical axial length in mm = AL + (0.65696 − 0.02029)AL;

$n_a$ = refractive index of the aqueous and the vitreous = 1.336;

$n_c$ = refractive index of the cornea = 1.333;

$n_cm1 = n_c - 1$;

R = targeted postoperative refraction in diopters;

r = average corneal radius of curvature in mm; and

V = the distance between the posterior surface of the lens and the apex of the cornea in m = 12.

As will be appreciated by those skilled in the art, the method of the present invention reduces the number of estimated constants and increases the accuracy of IOL implant power calculation, particularly for eyes having extremely short or long axial lengths.

This description is given for purposes of illustration and explanation. It will be apparent to those skilled in the relevant art that changes and modifications may be made to the invention as described without departing from its scope or spirit.

We claim:

1. A method of calculating a required power of an intraocular lens to be implanted in an eye, comprising the steps of:
    a) measuring an axial length, a preoperative anterior chamber depth and a natural lens thickness of the eye;
    b) measuring and averaging a corneal radii of curvature along a first axis and along a second axis normal to the first axis;
    c) calculating a lens locator constant from the axial length and the corneal radii of curvature using a quadratic surface equation;
    d) determining a postoperative anterior chamber depth using the preoperative anterior chamber depth, the natural lens thickness and the lens locator constant; and
    e) calculating the required power of the intraocular lens and a predicted postoperative refraction using the postoperative anterior chamber depth.

2. The method of claim 1 wherein the quadratic surface equation is in the form $J_{ind} = C_1AL + C_2AL^2 + C_3K_{ave} + C_4K_{ave}^2 + C_5K_{ave}* AL + C_6$, where $J_{ind}$ is the lens locator constant, $C_1$-$C_6$ are constants that are intraocular lens specific and determined by regressive data fitting, AL is the axial length of the eye to receive the intraocular lens and $K_{ave}$ is the corneal radii of curvature of the eye to receive the intraocular lens.

3. A method of calculating a required power of an intraocular lens to be implanted in an eye, comprising the steps of:
    a) measuring an axial length, a preoperative anterior chamber depth and a natural lens thickness of the eye;
    b) measuring and averaging a corneal radii of curvature along a first axis and along a second axis normal to the first axis;
    c) calculating a lens locator constant from the axial length and the corneal radii of curvature using a quadratic surface equation in the form $J_{ind} = -C_1AL + C_2AL^2 + C_3K_{ave} + C_4K_{ave}^2 + C_5K_{ave}* AL + C_6$, where $J_{ind}$ is the lens locator constant, $C_1$-$C_6$ are constants that are intraocular lens specific and determined by regressive data fitting, AL is the axial length of the eye to receive the intraocular lens and $K_{ave}$ is the corneal radii of curvature of the eye to receive the intraocular lens;
    d) determining a postoperative anterior chamber depth using the preoperative anterior chamber depth, the natural lens thickness and the lens locator constant; and
    e) calculating the required power of the intraocular lens and a predicted postoperative refraction using the postoperative anterior chamber depth.

* * * * *